United States Patent [19]

Rodriguez

[11] Patent Number: 5,800,561
[45] Date of Patent: Sep. 1, 1998

[54] POWER-ASSISTED UPPER EXTREMITY ORTHOSIS

[75] Inventor: David Rodriguez, Playa del Rey, Calif.

[73] Assignee: Massachusetts Institute of Technology, Cambridge, Mass.

[21] Appl. No.: 649,967

[22] Filed: May 15, 1996

[51] Int. Cl.⁶ .................. A61F 2/54; A61F 2/74
[52] U.S. Cl. .................. 623/26; 623/64; 601/40; 602/22
[58] Field of Search .................. 623/64, 63, 57, 623/58, 26, 25; 414/4; 901/38; 601/5, 33, 40; 602/22

[56] References Cited

U.S. PATENT DOCUMENTS

| | | |
|---|---|---|
| 2,429,866 | 10/1947 | Broste .................. 623/26 |
| 2,893,016 | 7/1959 | Zion . |
| 3,020,908 | 2/1962 | Daniels et al. . |
| 3,418,661 | 12/1968 | Allison et al. . |
| 3,631,542 | 1/1972 | Potter .................. 601/40 X |
| 3,694,021 | 9/1972 | Mullen .................. 414/4 X |
| 3,822,418 | 7/1974 | Yakobson et al. . |
| 3,923,166 | 12/1975 | Fletcher et al. . |
| 3,927,424 | 12/1975 | Itoh . |
| 3,967,321 | 7/1976 | Ryan et al. . |
| 4,046,262 | 9/1977 | Vykukal et al. . |
| 4,084,267 | 4/1978 | Zadina . |
| 4,167,044 | 9/1979 | Girard . |
| 4,180,870 | 1/1980 | Radulovic et al. .................. 623/26 |
| 4,364,593 | 12/1982 | Maeda . |
| 4,650,492 | 3/1987 | Barkhordar et al. . |
| 4,730,862 | 3/1988 | Caen et al. . |
| 4,745,812 | 5/1988 | Amazeen et al. . |
| 4,842,607 | 6/1989 | Repperger et al. . |
| 4,876,944 | 10/1989 | Wilson et al. . |
| 4,958,705 | 9/1990 | Horvath . |
| 4,990,162 | 2/1991 | LeBlanc et al. . |
| 5,020,790 | 6/1991 | Beard et al. . |
| 5,040,626 | 8/1991 | Paynter . |
| 5,101,472 | 3/1992 | Repperger . |
| 5,116,386 | 5/1992 | Scribner . |
| 5,258,038 | 11/1993 | Robinson et al. . |
| 5,282,460 | 2/1994 | Boldt . |

FOREIGN PATENT DOCUMENTS

| | | | |
|---|---|---|---|
| 408797 | 12/1966 | Australia .................. | 414/4 |
| 618786 | 4/1961 | Canada .................. | 623/26 |
| 717849 | 10/1966 | Italy .................. | 623/25 |
| 610522 | 6/1978 | U.S.S.R. .................. | 623/26 |

OTHER PUBLICATIONS

Janovsky F, Myoelectric control and driving system for hand orthoses, Biomedizinische Technik, 22 (1–2), 21–26, Jan.–Feb. 1977.

Nickel V L et al., Synthetically powered orthotic systems, The Journal of Bone and Joint Surgery, 47B (3), 458–464, Aug. 1965.

Primary Examiner—David H. Willse
Attorney, Agent, or Firm—Nutter, McClennen & Fish, LLP

[57] ABSTRACT

An orthotic device for a human forearm and hand is provided having first and second gripping members that are interposable between the thumb and fingers of a user's hand. An actuator moves one gripping member relative to the second gripping member in response to user input. The actuator of the orthotic device can include a gas piston driven by compressed gas. A valve controlling gas flow is actuated by an electric motor.

12 Claims, 5 Drawing Sheets

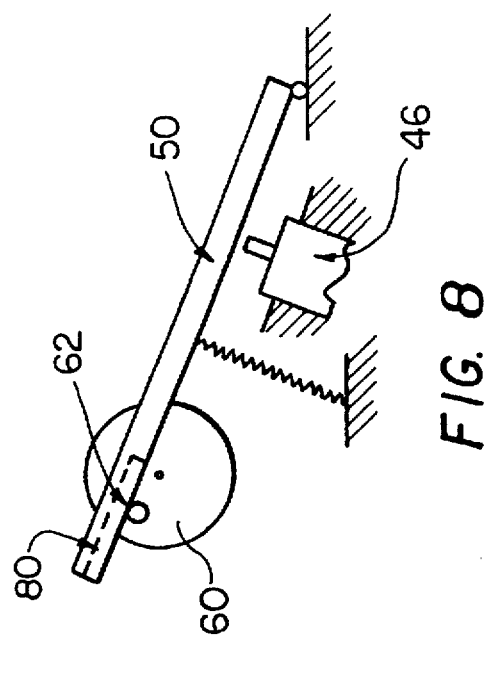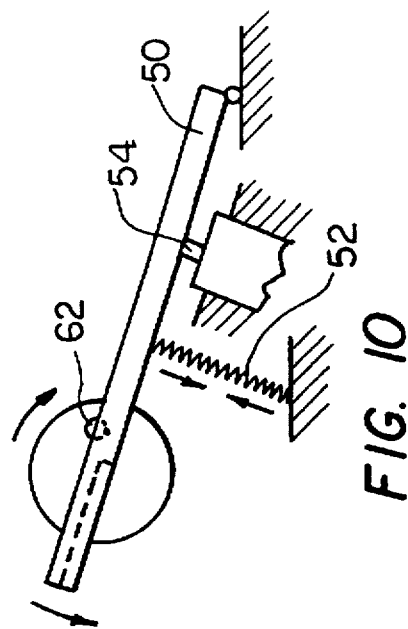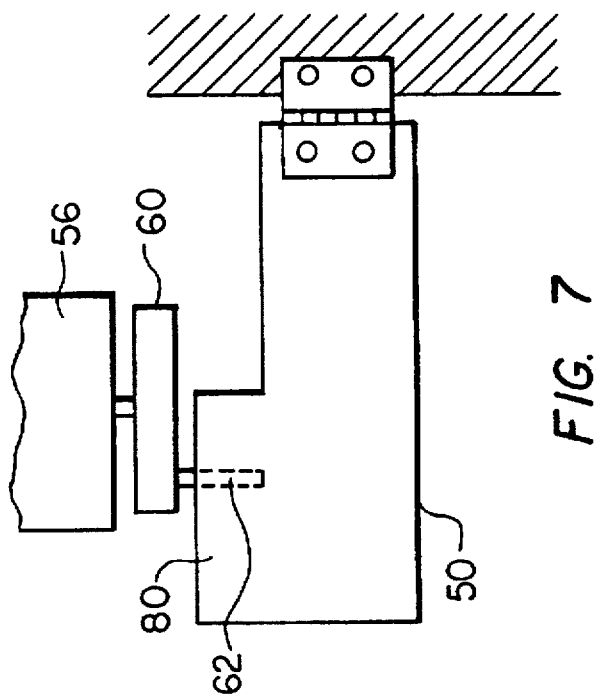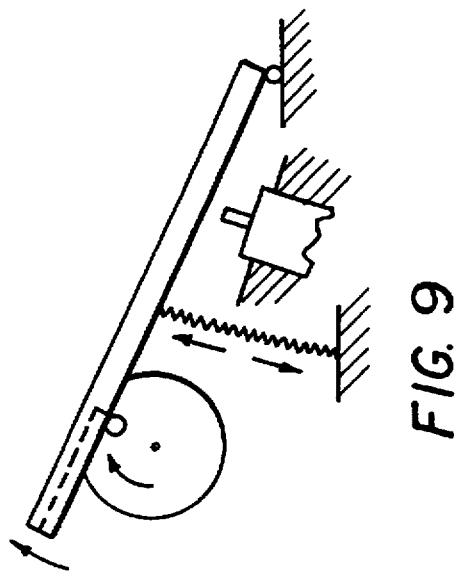

POWER-ASSISTED UPPER EXTREMITY ORTHOSIS

FIELD OF THE INVENTION

The invention relates to an orthotic device, and more particularly to a power assisted orthosis for arthritis patients.

BACKGROUND OF THE INVENTION

Rheumatoid arthritis is a joint disease which affects millions of individuals. A significant feature of rheumatoid arthritis is synovitis, which is the inflammation of the synovium. The synovium is a membrane that contains the lubricating fluid in articulating joints, which is the type usually affected by rheumatoid arthritis. Due to an abnormal reaction of the immune system, the synovium can become quite painful. If the inflamed synovium grows and spreads over the top of the joint cartilage, enzymes are produced that destroy collagen, the cartilage protein. When cartilage is roughened by this erosion, smooth joint motion is lost and a grating sensation at the joint is felt during movement. Subsequent swelling can cause the ligaments and tendons proximate the joint to stretch, thereby rendering the joint less stable. As pain discourages an arthritis sufferer from using the affected joint, muscles that move the joint atrophy from disuse. Eventually, ligaments can rupture and produce considerable deformity and loss of functionality of the affected joint.

Because the damage produced by rheumatoid arthritis accumulates over time and is not reversible, it is highly desirable that patients protect their joints as much as possible. Accordingly, many patients change their lifestyles drastically and avoid many normal activities from fear of increasing joint damage.

Numerous self-help devices exist to help arthritic people. However, many of the devices are adapted for one specific function such as opening a door or opening bottles and other containers, and the devices are usually installed or placed all around the home near the expected use location. Not only is it awkward and inconvenient to use numerous specialized devices, but it can be logistically tedious to function normally away from home.

As an alternative to single use apparatus, powered orthotic devices are known for moving a disabled hand. For example, U.S. Pat. No. 4,167,044 to Girard; 4,084,267 to Zadina; 3,967,321 to Ryan, et al.; and 3,020,908 to Daniels, et al. each disclose mechanisms for moving either or both of the fingers and thumb toward each other to provide a gripping action. However, each of these disclosures teaches a mechanism which pushes the fingers or thumb together. This results in substantial force being applied to the joints of the appendages of hand. Although such an arrangement may be acceptable for an individual suffering from complete or partial paralysis of the hand, it is unacceptable for an individual suffering from rheumatoid arthritis. Additionally, because these devices are intended for individuals with paralyzed hands, there is no provision for fingertip controls which would render an orthotic device for the hand easy and intuitive to use.

SUMMARY OF THE INVENTION

The present invention provides an upper extremity orthotic device for arthritis patients which transmits loads directly from gripped objects to the forearm, bypassing the vulnerable joints of the fingers and wrist. The easily donned and doffed device is controlled with a trigger mechanism operated by one or more fingers to provide an intuitive and user friendly interface. A pressurized gas supply and electric battery power the device which is relatively compact and lightweight.

In an exemplary embodiment, the orthotic device includes a first gripping member including a first gripping surface and a finger placement surface, and a second gripping member including a second gripping surface and a thumb placement surface. The second gripping surface opposes the first gripping surface and the second gripping member is movable with respect to the first gripping member. The first and second gripping members are interposed between the thumb and fingers of a human hand. An elongate member is secured to the second gripping member and is adapted for enclosing at least a portion of the user's forearm. An actuator moves the first gripping member relative to the second gripping member and a trigger mechanism on the finger placement surface of the first gripping member initiates activation of the actuator in response to user's touch of the trigger mechanism.

DESCRIPTION OF THE DRAWINGS

The invention will be more fully understood from the following detailed description taken in conjunction with the accompanying drawings in which:

FIG. 7 is a plan view of some control elements illustrated in FIG. 6;

FIG. 8 illustrates the first stage of a triggering sequence;

FIG. 9 illustrates the second stage of a triggering sequence;

FIG. 10 illustrates the third stage of a triggering sequence; and

DETAILED DESCRIPTION OF THE INVENTION

Figure 1:
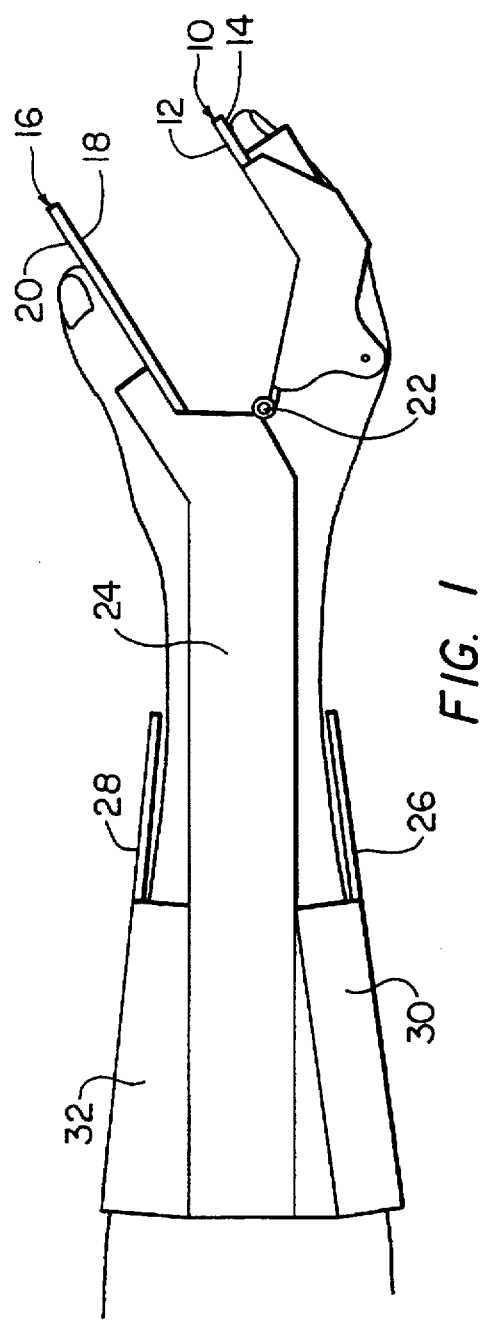
FIG. 1 is a side view of the power assisted orthotic device in accordance with the invention, showing the device in association with a user's hand and forearm.

FIG. 1 is a side view of an exemplary embodiment of a power assisted orthotic device in accordance with the invention, showing the device fitted to a user's hand and forearm. The device includes a gripping assembly having a first gripping member 10, a first gripping surface 12, and a finger placement surface 14. Opposing the first gripping member 10 is a second gripping member 16 having a second gripping surface 18 and a thumb placement surface 20. The first and second gripping members 10, 16 are movable with respect to each other. In the exemplary embodiment, the first and second gripping members 10, 16 are joined at a hinge-like joint 22 that is volar to the MP joints of the hand. It must be noted that the first and second gripping members 10, 16 are interposed between the user's thumb and fingers and that the thumb and fingers cannot be placed between the gripping members.

A stabilizing/force transfer assembly includes an elongate member 24 secured to one of the gripping members 10, 16. The elongate member 24 extends along the user's forearm to provide a lever arm for reducing the force generated by resisting torques at the gripping assembly when the device is used to rotate objects. In an exemplary embodiment, the elongate member 24 is immovably secured to the second gripping member 16 so that when the device is donned, a user's wrist assumes a slight dorsiflexion of about 20° and the elongate member extends along and over the radius bone of the forearm.

The elongate member 24 can be secured to or stabilized with respect to the user's forearm by encircling all or a portion of the forearm with a structure attached to or part of the elongate member and/or with one or more straps or bands. In the illustrated embodiment the elongate member 24 is provided with a first stabilizer 26 and a second stabilizer 28 that partially enclose the forearm. In the illustrated embodiment the first stabilizer 26 is on the dorsal forearm, and the second stabilizer 28 is on the volar forearm. The device can include resilient members 30 and 32 that link the first and second stabilizers 26 and 28, respectively, to the elongate member 24 to provide a secure and comfortable fitting device. This configuration is easily and quickly donned and doffed.

Figure 2:
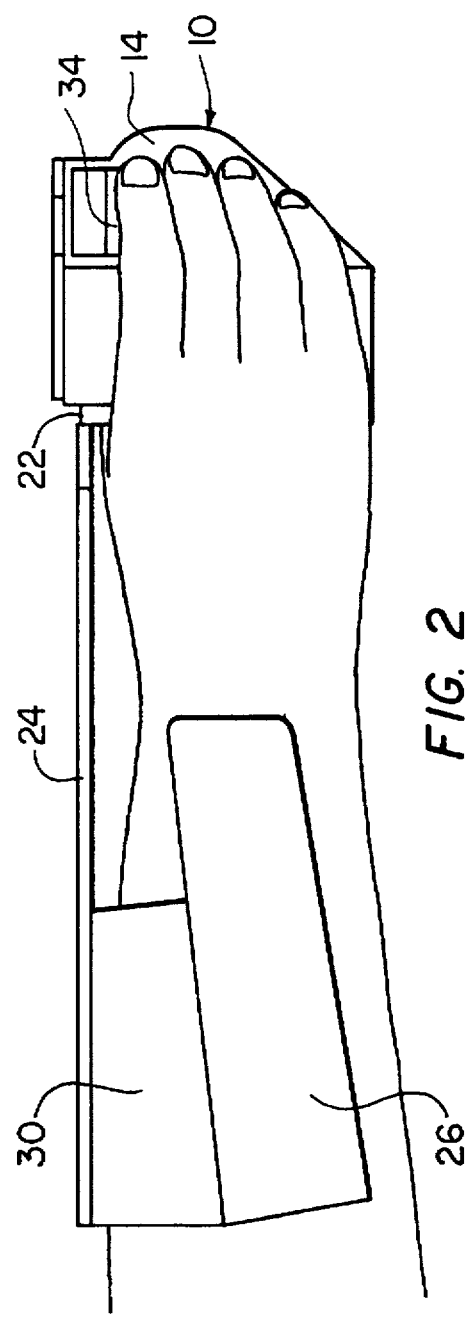
FIG. 2 is top view of the hand, forearm, and orthotic device of FIG. 1.

FIG. 2 is a top view of the orthotic device of FIG. 1 which more clearly shows the first stabilizer 26 and finger placement surface 14 on of the first gripping member 10. It will also be noted in this view that the axis of the hinge-like joint 22 is substantially perpendicular to the longitudinal axis of the elongate member 24. Also visible, but partially covered by the user's index finger, is a trigger mechanism 34 which when pressed initiates activation of an actuator that moves the first gripping member relative to the second gripping member.

Figure 3:
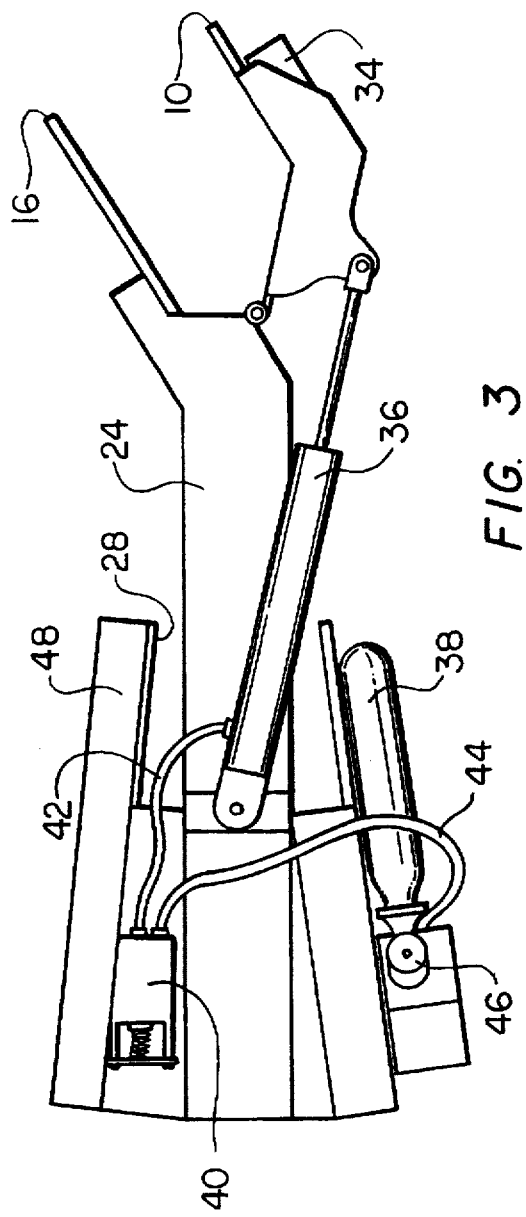
FIG. 3 is a side view showing additional features of the orthotic device in accordance with the invention.
Figure 4:
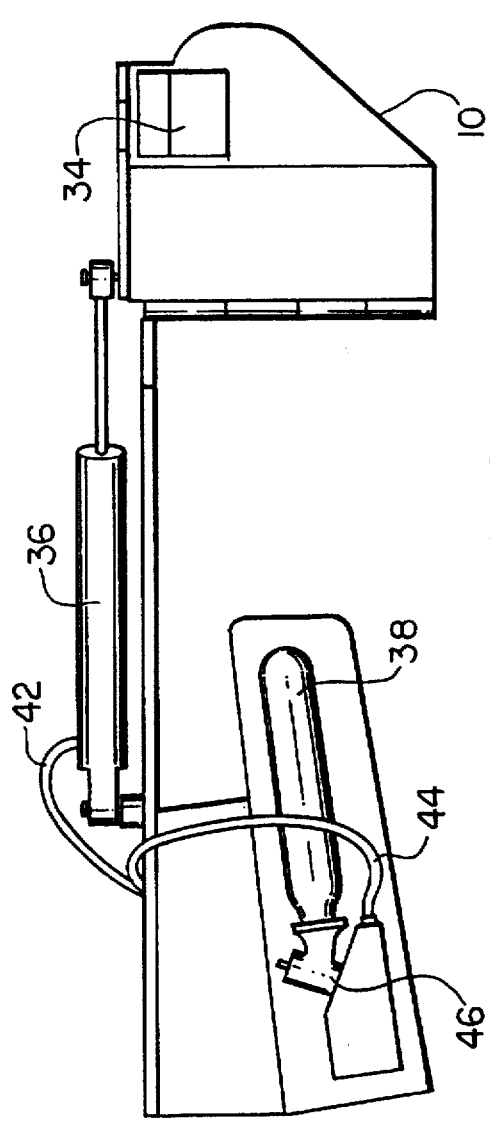
FIG. 4 is a top view of the orthotic device FIG. 3.
Figure 5:
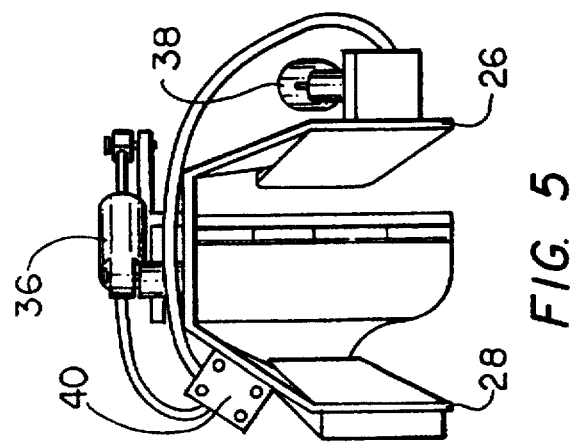
FIG. 5 is an end view of the orthotic device FIG. 3.

Referring now to FIGS. 3–5, additional features of the orthotic device are shown which provide for controlled relative movement of the first and second gripping members 10 and 16. FIG. 3, for example, illustrates an actuator 36, here a gas piston, that extends and retracts to move the first gripping member 10 with respect to the second gripping member 16. The actuator 36 could also be an electrical or an hydraulic device. One portion of the actuator 36 is secured to the elongate member 24 and a second portion of the actuator is secured to the first gripping member. Extension and retraction of the actuator 36 is initiated by pressing a trigger mechanism 34 that is in communication with one or more other control element described below. The trigger mechanism 34, which is readily accessible to one or more of a user's fingers, can be a simple two-position or on/off switch, however, any input device responsive to a user's finger is acceptable.

Continuing to refer to FIGS. 3–5, the actuator 36 is in communication with a power supply. As this embodiment includes a gas powered actuator, the power supply includes a pressurized gas cylinder 38. In one embodiment, the pressurized gas cylinder is a compressed carbon-dioxide cartridge. Standard 12 gram $CO_2$ cartridges are particularly advantageous as they are readily available, cheap, light weight, and compact. Advantageously, the gas pressure from these cartridges remains substantially constant even after gas has been released from the cartridge repeatedly. A relief valve 40 is interposed between the actuator 36 and the gas cylinder 38. A gas tube 42 connects the relief valve 40 with the actuator 36; and a gas tube 44 connects the relief valve 40 to a trigger valve 46 associated with the gas cylinder 38. A battery pack 48 for powering an electrical circuit is conveniently secured to the second stabilizer 28.

Figure 6:
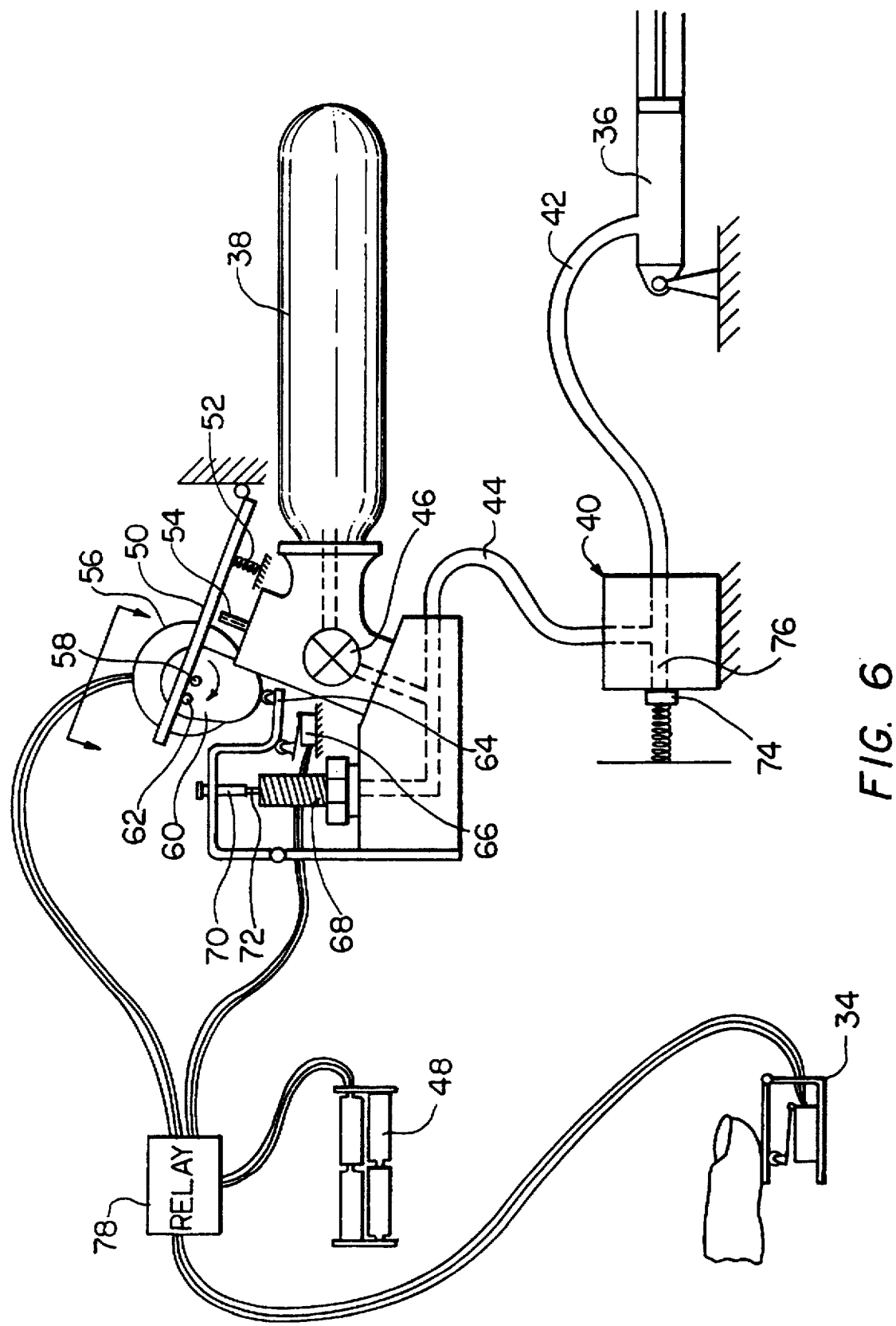
FIG. 6 is a schematic view of a power and control system for the orthotic device.

FIG. 6 is a schematic illustration of additional devices for activating, powering, and controlling movement of the actuator in response to user input. FIG. 6 also shows additional details with respect to an exemplary trigger valve 46 and relief valve 40. As illustrated, the trigger valve 46 is actuated by a hammer 50 that is biased by a hammer spring 52; a valve pin 54 accessible to said hammer; and an electric motor 56 having a shaft 58 coupled to a cam 60. A trigger pin 62 is mounted to said cam 60 so that rotation of the cam from a first position to a second position by the -electric motor 56 causes the trigger pin to engage and move the hammer 50. A cam follower arm 64 moves as the cam 60 rotates to actuate a microswitch 66 and to open and close a control valve 68. The control valve 68 includes an adjustment screw 70 aligned with a pin 72 that is biased toward the screw. The control valve 68 is open when the pin 72 is depressed and is closed when the pin is extended.

The pressure relief valve 40 includes a biased element 74 that is pushed away from an opening 76 in the pressure relief valve when the gas pressure within the pressure relief valve exceeds the bias force applied to the biased element. When the pressure drops below a predetermined level, the biased element 74 seals the opening 76 in the pressure relief valve 40.

An electrical circuit includes a relay switchboard 78 in electrical communication with the battery pack 48, the trigger mechanism 34, the cam microswitch 66, and the electric motor 56.

The orthotic device functions in the following manner. In a first or rest state, the control valve 68 is open, and the actuator 36 can be moved to open and close the grip with very little effort. When the trigger mechanism 34 is depressed, the electric motor 56 causes the cam 60 to rotate, thereby closing the control valve 68 and allowing the hammer to be lifted and released so as to impact the valve pin 54, causing a puff of $CO_2$ to flow to the piston of the actuator 36. When the trigger mechanism 34 is released, the control valve 68 opens and the $CO_2$ in the system escapes therefrom.

Referring now to FIGS. 7–10, additional details of the hammer and valve pin configuration are shown. FIG. 7 illustrates a configuration of the hammer 50 including an enlarged portion 80 that engages the trigger pin 62 on the cam 60 until the electric motor 56 causes the cam and trigger pin to rotate to a point where the enlarged portion does not engage the trigger pin. FIGS. 8 and 9 illustrate rotation of the cam, wherein the trigger pin is engaged with the enlarged portion of the hammer. FIG. 10 illustrates the cam rotated to disengage the trigger pin 62 from the hammer 50 and the hammer spring 52 pulling the hammer against the valve pin 54.

When the orthotic device is in the first state or at rest, the cam microswitch 66 is open, the control valve 68 is open, and the trigger pin 62 is below the enlarged portion 80 of the hammer. In this position the hammer 50 cannot be pushed against the trigger valve. In a second state, when the trigger mechanism 34 is actuated, the electric motor 56 rotates the cam 60 and the trigger pin 62. The trigger pin 62 starts to push the hammer 50 and loads the hammer spring 52 while the cam follower arm 64 closes the control valve 68 and the cam microswitch 66 to disconnect the electric motor 56 from the electrical power in accordance with the logic of the relay 78. Even after power to the electric motor 56 is terminated, there is sufficient inductance in the motor to keep rotating the cam and trigger pin to clear the hammer enlarged 80, causing the hammer 50 to impact the pin 54 and release gas to the actuator 36.

Figure 11:
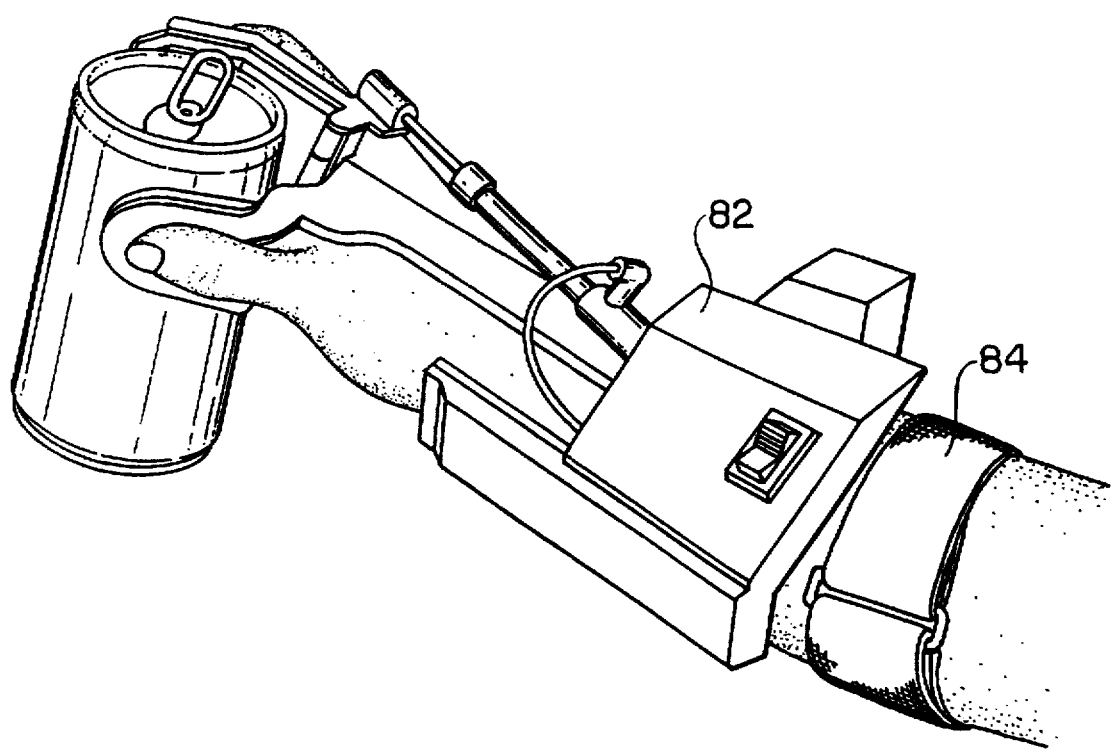
FIG. 11 is a perspective view of an embodiment of the invention showing an object being grasped.

FIG. 11 is a perspective view of an embodiment of the orthotic device having a housing 82 that covers the above described power and control elements. In the illustration, a can is being grasped with the aid of the device. Padding on surfaces of the device that contact the user's body makes the device more comfortable to wear and dispersed pressure over the skin to avoid pressure sores. An adjustable strap is secured to the dorsal side of the device to better secure it to the user's forearm. Additionally, the first and second gripping surfaces 12 and 18 can be textured or provided with a surface that improves or provides non-slip grasping.

Although the invention has been shown and described with respect to exemplary embodiments thereof, various other changes, omissions and additions in further detail thereof may be made therein without departing from the spirit and scope of the invention.

What is claimed is:

1. An orthotic device to be worn on a human forearm, hand, fingers and thumb comprising:

a first gripping member including a first gripping surface and a finger placement surface;

a second gripping member including a second gripping surface and a thumb placement surface, said second gripping surface opposing said first gripping surface, said first gripping member being movable with respect to said second gripping member, and said first gripping member and said second gripping member being interposable between said thumb and fingers of said human hand; and an elongate member immovably secured to one of said first and said second gripping members;

an actuator in communication with one of said first and said second gripping members, said actuator capable of moving said first gripping member relative to said second gripping member;

a cylinder of compressed gas for powering said actuator, said cylinder being mounted to the rest of said orthotic device, said cylinder sized substantially smaller than said device; and a trigger mechanism on said finger placement surface of said first gripping member, said trigger mechanism in communication with said actuator.

2. The device of claim 1, wherein said elongate member is adapted for enclosing at least a portion of said forearm.

3. The device of claim 1, wherein said device further includes a dorsal stabilizer and a volar stabilizer secured to said elongate member.

4. The device of claim 3, wherein said dorsal stabilizer and said volar stabilizer are secured to said elongate member by respective resilient members.

5. The device of claim 4, wherein said first gripping member and said second gripping member are joined at a hinge that defines an axis of rotation for one of said first and said second gripping members.

6. The device of claim 5, wherein said elongate member has a longitudinal axis perpendicular to said axis of rotation defined by said hinge.

7. The device of claim 1, wherein said actuator is a gas piston and further including:

a valve responsive to said trigger mechanism to control outflow of gas from said cylinder of compressed gas to said gas piston.

8. The device of claim 7, further comprising a pressure relief valve in-line between said valve and said actuator.

9. The device of claim 7, wherein said valve includes a pin movable from a first position to a second position to release gas from said cylinder of compressed gas.

10. The device of claim 9, further comprising a hammer movable from a first position to a second position to move said pin.

11. An orthotic device for a human forearm, hand, fingers and thumb comprising:

a first gripping member including a first gripping surface and a finger placement surface;

a second gripping member including a second gripping surface and a thumb placement surface, said second gripping surface opposing said first gripping surface, said first gripping member being movable with respect to said second gripping member, and said first gripping member and said second gripping member being interposable between said thumb and fingers of said human hand; and an elongate member immovably secured to one of said first and said second gripping members;

an actuator in communication with one of said first and said second gripping members, said actuator capable of moving said first gripping member relative to said second gripping member;

a trigger mechanism proximate said finger placement surface of said first gripping member, said trigger mechanism in communication with said actuator;

wherein said actuator is a gas piston and further including a source of compressed gas; and a valve responsive to said trigger mechanism to control outflow of gas from said source of compressed gas to said gas piston;

wherein said valve includes a pin movable from a first position to a second position to release gas from said source of compressed gas;

a hammer movable from a first position to a second position to move said pin; and an electric motor responsive to said trigger mechanism and a cam coupled to said electric motor and releasably engaged with said hammer, wherein rotation of said cam from a first point to a second point by said electric motor causes said hammer to be engaged with said cam and biased away from said pin, and wherein rotation of said cam from said second point to a third point causes said hammer to be disengaged from said cam allowing said hammer to impact said pin and move said pin from said first position to said second position.

12. An orthotic device for a human forearm, hand, fingers and thumb comprising:

a first gripping member including a first gripping surface and a finger placement surface;

a second gripping member including a second gripping surface and a thumb placement surface, said second gripping surface opposing said first gripping surface, said first gripping member being movable with respect to said second gripping member, and said first gripping member and said second gripping member being interposable between said thumb and fingers of said human hand;

an elongate member immovably secured to said second gripping member;

an actuator including a gas piston, said actuator anchored at a first end to said first gripping member and at a second end to said elongate member, said actuator extendable to move said first gripping member toward said second gripping member;

a trigger mechanism proximate said finger placement surface of said first gripping member;

a source of compressed gas;

a valve responsive to said trigger mechanism to control outflow of gas from said source of compressed gas to said gas piston, said valve including a pin movable from a first position to a second position to release gas from said source of compressed gas;

a hammer movable from a first position to a second position to move said pin;

an electric motor responsive to said trigger mechanism; and a cam coupled to said electric motor, said cam being releasably engaged with said hammer, wherein rotation of said cam from a first point to a second point by said electric motor causes said hammer to be engaged with said cam and biased away from said pin, and wherein rotation of said cam from said second point to a third point causes said hammer to be disengaged from said cam allowing said hammer to impact and move said pin from said first position to said second position.

* * * * *